US007635358B2

(12) United States Patent
Tan

(10) Patent No.: US 7,635,358 B2
(45) Date of Patent: Dec. 22, 2009

(54) MEDICAL DEVICE HAVING ANTI-MICROBIAL PROPERTIES AND A FALSE LUMEN AND METHOD OF MAKING THE SAME

(75) Inventor: Sharon Mi Lyn Tan, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 475 days.

(21) Appl. No.: 10/688,224

(22) Filed: Oct. 15, 2003

(65) Prior Publication Data

US 2005/0085777 A1    Apr. 21, 2005

(51) Int. Cl.
*A61M 5/32* (2006.01)
(52) U.S. Cl. .................................................... 604/265
(58) Field of Classification Search ......... 604/264–266, 604/269, 523, 4.01, 6.16, 29, 43, 507, 508, 604/93.01; 600/1–7
See application file for complete search history.

(56) References Cited

U.S. PATENT DOCUMENTS

| | | | |
|---|---|---|---|
| 4,623,329 A * | 11/1986 | Drobish et al. ................. 604/29 |
| 5,004,455 A | 4/1991 | Greenwood et al. |
| 5,059,186 A | 10/1991 | Yamamoto et al. |
| 5,269,755 A | 12/1993 | Bodicky |
| 5,411,550 A | 5/1995 | Herweck et al. |
| 5,562,652 A * | 10/1996 | Davis ....................... 604/890.1 |
| 5,567,495 A | 10/1996 | Modak et al. |
| 6,280,423 B1 | 8/2001 | Davey et al. |
| 6,319,226 B1 | 11/2001 | Sherry |
| 6,598,127 B2 * | 7/2003 | Matsubara et al. ........... 711/137 |
| 6,645,135 B1 * | 11/2003 | Bhat .............................. 600/3 |
| 2004/0230162 A1 * | 11/2004 | Tan ............................. 604/171 |
| 2004/0230177 A1 * | 11/2004 | DiMatteo et al. ............ 604/523 |
| 2005/0055012 A1 * | 3/2005 | Trerotola ..................... 604/508 |

FOREIGN PATENT DOCUMENTS

EP          0381062 A2    8/1990
WO      WO 00/74743    * 12/2000

* cited by examiner

*Primary Examiner*—Nicholas D Lucchesi
*Assistant Examiner*—Laura A Bouchelle
(74) *Attorney, Agent, or Firm*—Mayer & Williams PC; David B. Bonham; Keum J. Park

(57) ABSTRACT

A medical device with anti-microbial properties to prevent infections. This medical device, such as an in-dwelling catheter, has a portion that is insertable into the body of a patient and accessible from outside the body once the portion is inserted. The portion has an outer wall, a first active lumen within the outer wall, and a false lumen within the outer wall in which the false lumen has a distal portion and a proximal portion. The false lumen contains an anti-microbial agent that provides the outer wall with anti-microbial properties. The distal portion of the false lumen is sealed. The false lumen may be adjacent to the first active lumen. The medical device may also contain a second active lumen, wherein the first active lumen is an inlet lumen and the second active lumen is an outlet lumen. Alternatively, the false lumen may surround the first active lumen.

26 Claims, 3 Drawing Sheets

MEDICAL DEVICE HAVING ANTI-MICROBIAL PROPERTIES AND A FALSE LUMEN AND METHOD OF MAKING THE SAME

FIELD OF THE INVENTION

The invention generally relates to medical devices that are inserted into the body of a patient. More particularly, the invention is directed to medical devices with anti-microbial properties as well as a false lumen and methods for making such medical devices having anti-microbial properties.

BACKGROUND OF THE INVENTION

Implanted medical devices such as venous and arterial catheters, neurological prostheses, wound drains, urinary "Foley" catheters, peritoneal catheters, and other luminal in-dwelling devices, have been useful for treating various medical conditions. However, a drawback of implanted medical devices is the risk of infection while the medical device is inserted in the body, and thereafter. Such risk exists even though the medical devices are sterilized and carefully packaged to guard against introduction of microbes or pathogens during implantation or insertion of the medical device. For example, there is a risk of serious nosocomial infections when using catheters for hemodialysis procedures. In fact, central venous catheters account for most nosocomial catheter-related bloodstream infections.

When catheters and other in-dwelling luminal devices are inserted into body cavities such as the urinary tract, venous or arterial vessels, bacteria or other microbes can be picked up from the skin and carried into the insertion site where bacterial or microbial colonization may ensue. Infections may derive from an interaction of the microbes and the catheter micro-surface. Once infected, the microorganisms adhere to the catheter micro-surface and rapidly become encased in a polysaccharide matrix or biofilm, which protects the microorganisms from a host's defenses.

In the case of urinary and venous catheters, there is a significant threat of microbial growth along the exterior surface or outer wall of the catheter and, especially for catheters used long-term, there is a significant threat of microbial growth along the interior surface or inner wall. This can lead to chronic urinary tract infections (CUTI), or septicemia in the case of venous and arterial catheters, thrombolytic emboli, stenosis, and thrombosis resulting from infections, and other life threatening complications, especially among the elderly and immuno-compromised patients. Thus, there is a need for the development of better methods of preventing and treating infections caused by the insertion of catheters into a patient's body.

There have been many attempts to prevent such infections. For example, central venous catheters have been developed with chlorohexidine and silver sulfadiazine coatings (ArrowG+ard) and with a combination of minocycline and rifampin coatings (see, e.g., Cook Spectrum™). However, these antiseptic/antibiotic-impregnated catheters have not been adequate, as they have only been shown to reduce the incidence of catheter related infections in the short term, such as less than 14 days. Thus, there is a need for improved catheters that are effective in reducing infections in the long-term.

Iodine-based interventional devices have also been used to minimize the risk of nosocomial bloodstream infection. In particular, an iodine-based, soft, flexible poly-carbonate fiber in the shape of a rod has been placed inside of in-dwelling catheters, as discussed in WO 00/74743 A1. Generally, these polymeric-matrices are chemically and geometrically configured to enable a controlled-release of monomeric iodine at specific conditions such as temperature, making them extremely useful as anti-infective substrates for the effective management of catheter-based nosocomial blood stream infections. Since the catheter polymer is semi-permeable, the iodine can egress to the exterior surface of the in-dwelling catheter.

Such iodine-loaded rod is inserted into a catheter by gently sliding the rod into the inlet and outlet ports of a lumen of the catheter through which body fluids flow. During insertion, the rod is held between the thumb and index fingers of the person inserting the rod. Due to the flexibility of the rod, resistance may be encountered while gently threading it into the lumen. Inserting this rod into the catheter, without contamination, is an arduous and challenging exercise. Even with the use of gloves, there is a potential for contamination. Also, during a dialysis treatment, the iodine rod has to be removed from the lumen through which body fluid flows. New iodine rods are inserted after completion of this dialysis. With multiple insertions and removals of the rods from the lumen, which is in contact with body fluids, there is an increased risk of contamination. It would be desirable to have a medical device comprising an anti-microbial substrate that would not have to be removed and reinserted during every dialysis treatment, and which is not in contact with body fluids, i.e., independent of the inlet and outlet lumens.

However, generally, the distal tips of catheters have open ends so that body fluid such as blood can enter and exit the catheter lumens. Use of iodine rods with such catheters having open ends can be problematic. For example, blood clots could form at the open ends of the catheter tip and hinder the insertion of the iodine rod. In addition, iodine is directly released into the body or bloodstream through the open tip. Thus, it would be desirable to have a catheter designed to be effectively used with a substrate having anti-microbial properties. It would also be desirable to prevent iodine in the lumen from escaping directly through the open catheter tip and into the body, yet deliver iodine into the inlet and outlet lumens. Moreover, it would be desirable to be able to control the release of iodine into the body.

Accordingly, there is a need for a medical device that has a portion that can be inserted into the body of a patient and that can more effectively provide anti-microbial activity. In particular, there is a need for a medical device that can provide anti-microbial properties without requiring repeated insertions and removals of an anti-microbial substrate that could introduce contamination. There is also a need for a medical device that can provide long-term anti-microbial or anti-infection activity. There is also a need for an improved method of making such medical devices.

SUMMARY OF THE INVENTION

These and other objectives are accomplished by the present invention. The present invention is directed to a medical device with anti-microbial properties. The medical device comprises a catheter that has a portion that is partially insertable into the body of a patient and accessible from outside the body once the portion is inserted. The portion has an outer wall, at least one active lumen within the outer wall, and a false lumen within the outer wall. The false lumen has a distal portion and a proximal portion. In addition, the false lumen contains an anti-microbial agent that provides the outer wall with anti-microbial properties. The distal portion of the false lumen is sealed, and the active lumen at least partially surrounds the false lumen.

In another embodiment, the present invention is a medical device with anti-microbial properties. The medical device has a portion that is partially insertable into the body of a patient, and accessible from outside the body once the portion is inserted. In this embodiment, the portion has an outer wall, at least one active lumen within the outer wall, and a false lumen within the outer wall. The false lumen has a distal portion and a proximal portion. The distal portion of the false lumen is sealed. The medical device further comprises a substrate having a first end and a second end. The substrate is comprised of an anti-microbial agent, and is capable of being inserted into the false lumen. The substrate is also capable of providing the outer wall with anti-microbial properties.

In yet another embodiment, the present invention is a medical device with anti-microbial properties. The medical device has a portion that is partially insertable into the body of a patient and accessible from outside the body once the portion is inserted. The portion has an outer wall, a first active lumen within the outer wall, and a false lumen within the outer wall. The false lumen has a distal portion and a proximal portion. The false lumen contains an anti-microbial agent that provides the outer wall with anti-microbial properties. The distal portion of the false lumen is sealed. The first active lumen and the false lumen are separated by an active lumen wall comprised of a non-permeable material.

Thus, the present invention provides for medical devices that can prevent or reduce the incidences of infection during use of the medical devices. The medical device is designed to prevent an anti-microbial agent in the false lumen from escaping directly into the body and to control the release of such anti-microbial agent into the body. In addition, the medical device provides anti-microbial activity at the site of the implanted medical device without requiring repeated insertions and removals of an anti-microbial substrate.

DESCRIPTION OF THE PREFERRED EMBODIMENTS

Figure 1:
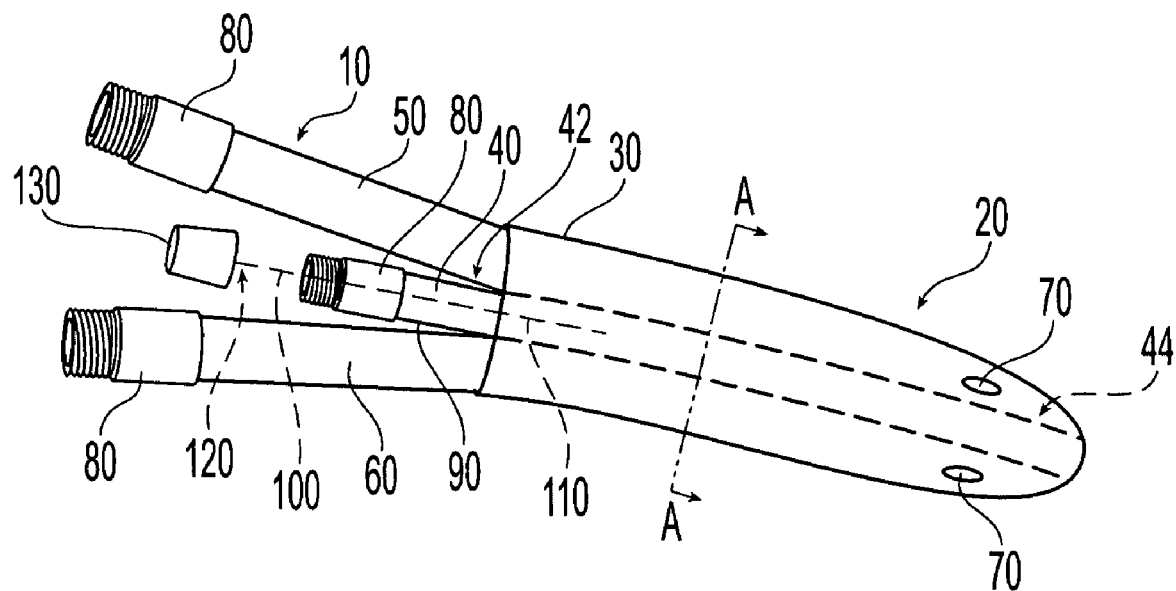
FIG. 1 illustrates a medical device of the present invention. In this embodiment, the medical device is a catheter that has an outer wall and includes therein a false lumen (in dotted lines) having a proximal portion and a distal portion, and an outlet lumen and an inlet lumen. The distal portion of the false lumen is sealed. Unlike the false lumen, the ends of the outlet lumen and inlet lumen are not sealed. A substrate comprising an anti-microbial agent is disposed in the false lumen.

The medical device of the present invention generally comprises an elongated shaft that extends along a longitudinal axis between the proximal portion 10 and the distal portion 20 of the medical device. The medical device has an outer wall 30 or a wall that is exposed to body tissue when the medical device is inserted into the body. The outer wall 30 surrounds at least one interior passageway or active lumen which extends along the longitudinal axis. An active lumen is a lumen that is essential to carrying out or performing the function or purpose of the medical device. For instance, in a hemodialysis catheter active lumens are the inlet lumen and outlet lumen.

Also within the outer wall 30 of the medical device is a false lumen 40. The false lumen 40 has a proximal portion 42 and a distal portion 44 and extends along the longitudinal axis of the medical device. The false lumen 40 is sealed at the distal portion 44 of the false lumen 40.

A false lumen 40 is a lumen this is not essential to the functioning or performance of the medical device. Although the false lumen 40 can enhance the medical device, such as provide anti-microbial properties, it is not necessary to performing the principle function of the medical device. The false lumen 40 is a lumen which is not used in the main function of the catheter but which is for a separate secondary function. In particular, the false lumen 40 is used to deliver the anti-microbial agents to the device. In addition, the false lumen 40 does not have an opening at the end of the distal portion 44.

In one embodiment, the false lumen 40 is disposed adjacent to a first active lumen 50. Preferably, the medical device also includes a second active lumen 60 that is also adjacent to the false lumen 40 as shown in FIG. 1. The first active lumen 50 and the second active lumen 60 preferably at least partially surround the false lumen 40. The first active lumen 50 may be an inlet lumen and the second active lumen 60 may be an outlet lumen, such as in a hemodialysis catheter or other dual lumen catheters. FIG. 1 shows a catheter having a first active lumen 50 that is an inlet lumen and a second active lumen 60 that is an outlet lumen. The inlet and outlet lumens are adjacent to the false lumen 40. Each lumen has a hub 80 at the proximal portion 10 of the medical device. Unlike the false lumen 40, the outlet lumen and the inlet lumen are not sealed at the distal portion 20 of the catheter, but having openings 70.

Figure 2:
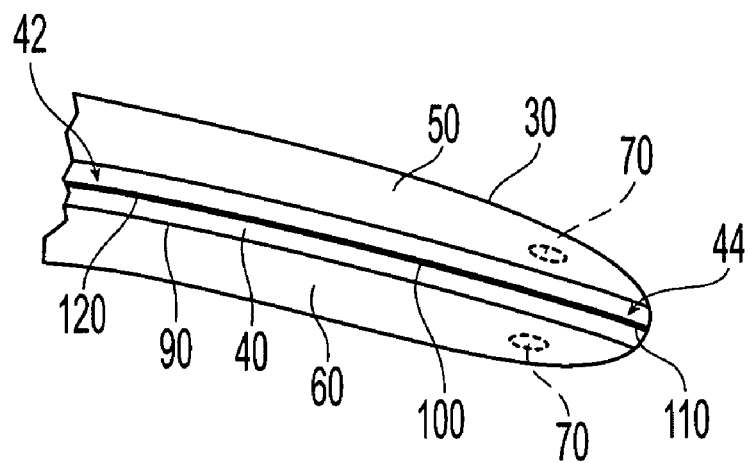
FIG. 2 illustrates a cross-sectional view along the longitudinal axis of the distal portion of the medical device of FIG. 1. This figure shows a false lumen, an outlet lumen and inlet lumen that are adjacent to the false lumen, and a substrate comprising an anti-microbial agent that is disposed in the false lumen.

FIG. 2 shows a cross-sectional view along the longitudinal axis of the distal portion 20 of the medical device of FIG. 1. As seen in FIG. 2, in this embodiment the false lumen 40, the first active lumen 50, and the second active lumen 60 are disposed parallel to each other. A false lumen wall 90 defines the false lumen 40.

Figure 3:
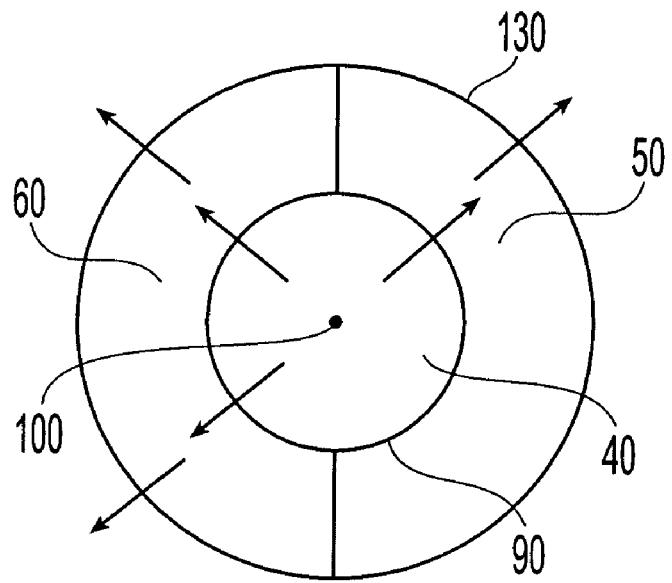
FIG. 3 illustrates a cross-sectional view of FIG. 1 at line A-A.

FIG. 3 shows a cross-sectional view along the line marked A-A of the medical device in FIG. 1. As shown in FIG. 3, the first active lumen 50 and the second active lumen 60 each partially surrounds the false lumen 40. In alternative embodiments, the false lumen 40 can be surrounded by a single active lumen or more than two active lumens.

Figure 4:
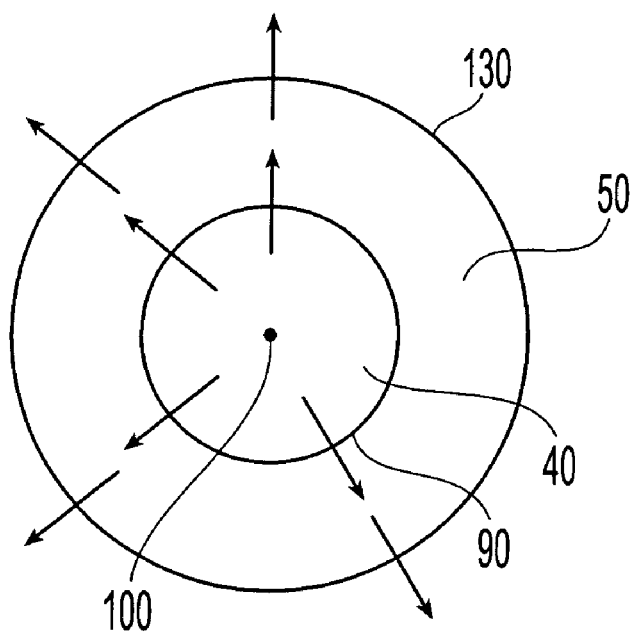
FIG. 4 illustrates a cross-sectional view of a medical device of the present invention having a first active lumen surrounding a false lumen.

For example, FIG. 4 shows a cross-sectional view of another embodiment in which a first active lumen 50 surrounds the false lumen 40. Although the false lumen 40 and the first active lumen 50 are shown to be concentric in FIG. 4, they need not be concentric. For example, the false lumen 40 may be off-centered.

The false lumen 40 and the active lumen may also include a locking mechanism at the proximal portion 10 of the medical device. Preferably, the locking mechanism on the false lumen 40 is different from the locking mechanism on the active lumen to prevent insertion of a substrate containing an anti-microbial agent into an active lumen. Thus, this design would prevent misuse and the accidental insertion of the anti-microbial agent into the inlet and/or outlet lumens and delivery of the anti-microbial agent through the inlet and/or outlet lumens and into the body.

The medical device of the present invention has a portion that is partially insertable into the body of a patient. In addition, the portion is accessible from outside the body once the portion is inserted into the body. Suitable medical devices include, for example, catheters. Any catheter used for medical treatment can generally be used for the present invention. Suitable catheters include, but are not limited to, venous, arterial, urinary "Foley" catheters, wound drains, peritoneal catheter, percutaneous catheters, sheaths and trocars, drainage catheters, endoscopes and endoscopic catheters, and gastrointestinal catheters. In addition to catheters, other medical devices that have at least one lumen and are insertable into the body of a patient and accessible through the skin or other method once implanted can be used in the present invention. For example, the following other luminal in-dwelling medical devices may be used: cannulas, cardiac pacemaker leads or lead tips, cardiac defribrillator leads or lead tips, implantable vascular access ports, blood tubing, vascular or other grafts, intra-aortic balloon pumps, heart valves, cardiovascular sutures, total artificial hearts and ventricular assist pumps.

Such medical devices may be made of any suitable material as known to one skilled in the art. For example, the medical devices suitable for the present invention may be fabricated from polymeric materials. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Preferably, the medical device is made from a polymer, such as polyethylene, polyurethane, polycarbonates, ethyl vinyl acetate, polyamides, polyimides, PEBAX or similar material. The medical device may be made by any method known to one skilled in the art. Suitable materials for the false lumen 40 include, but are not limited to, polyurethane, silicone or polycarbonate.

The medical device of the present invention also comprises an anti-microbial agent that provides the outer wall 30 with anti-microbial properties. The anti-microbial agent is disposed in the false lumen 40 of the medical device. Suitable anti-microbial agents include, but are not limited to, elemental iodine (also called free iodine), hypohalites, haloamines, thiocyanogen, hypothiocyanite, silver ions, triclosan, antibiotics such as penicillin and amoxycillan, and rapromycin. Preferably, the anti-microbial agent is an iodine-based substance. The false lumen 40 is sealed so as to prevent the anti-microbial agent contained therein from directly entering into the body or bloodstream. Therefore, the concentration of the anti-microbial agent released into the body is controlled.

The medical device may further comprise a substrate 100 containing the anti-microbial agent therein. The substrate 100 has a first end 110 and a second end 120. Preferably, the substrate 100 is in the shape of a rod or tube so that it can easily be inserted into the false lumen 40 of the medical device. The substrate 100 is inserted into the false lumen 40 of the medical device such that the first end 110 is positioned closer to the distal portion 44 of the false lumen 40 than the second end 120. Preferably, the second end 120 reaches the end of the distal portion 44 of the false lumen 40. In FIG. 1, a substrate 100 in the form of a rod is being inserted into a false lumen 40 through the hub 80 of the false lumen 40. Substrate 100 could also be in a liquid form of the anti-microbial agent instead of being in the form of a rod. In such case, the anti-microbial agent in the false lumen 40 will egress into the catheter walls.

The substrate 100 can be formed from the anti-microbial agent. For example, the substrate 100 may be made of an iodine-polycarbonate material. Alternatively, the substrate 100 can be formed from a material that does not contain an anti-microbial agent. For example, the material may be a polymer that is biodegradable or non-biodegradable. In addition, the polymer that may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biological agent or a suitable mixture of any of these, for example.

Preferred materials for the substrate 100 include, but are not limited to, polyurethane, polycarbonate, silicone, ethyl vinyl acetate, polypropylene, polyamides, polyimides, PEBAX or similar material, and co-polymers thereof.

The amount of the anti-microbial agent can be varied according to the desired effect. Also, the substrate 100 may have a greater amount of the anti-microbial agent at the first end 110 than at the second end 120. However, a uniform amount of the anti-microbial agent along the substrate 100 is preferred. The manufacture of the substrate 100 and the use of the substrate 100 for providing anti-microbial activity is described in WO 00/74743 A1.

FIG. 1 shows an embodiment of the present invention in which the substrate 100 is partially inserted into the false lumen 40. To protect and hold the substrate 100 in place during insertion of the substrate 100 into the false lumen 40 of the catheter, a connector such as a cap 130 is attached to the second end 120 of the substrate 100. The substrate 100 may be inserted into the false lumen 40 by handling the cap 130 instead of direct handling of the substrate 100 itself in order to avoid contamination and reduce the risk of introducing infection into the catheter. The cap 130 may be removably attached to the substrate 100 so that after the substrate 100 is inserted, the cap 130 may be detached from the substrate 100. However, preferably, the cap 130 remains attached to the substrate 100 for ease of removal of the substrate 100. The connector or cap 130 may be made of any suitable materials as known to one skilled in the art.

An aqueous solution is preferably contained in the false lumen 40 of the catheter or medical device. The aqueous solution may be any solution that can serve as a release medium for the anti-microbial agent. Suitable solutions include, but are not limited to, saline, heparinized saline, and sterile water. Once the substrate 100 containing the anti-microbial agent is positioned in the false lumen 40, the anti-microbial agent is exposed to the aqueous solution. The aqueous solution allows the anti-microbial agent, such as iodine, to be released from the substrate 100. As the iodine or other anti-microbial agent diffuses out of the substrate 100, the aqueous solution enables the iodine or anti-microbial agent to proliferate along the entire length of the false lumen 40. The anti-microbial agent is released into the false lumen 40. In addition, the anti-microbial agent itself may be in the liquid form and injected into the false lumen 40, and then the false lumen 40 may be capped.

The anti-microbial agent present in the false lumen 40 is allowed to diffuse through the wall 90 of the false lumen 40 and into the active lumens, i.e., inlet lumen and outlet lumen. Thereafter, the anti-microbial agent diffuses from the active lumens through the outer wall 30 of the medical device to provide anti-microbial activity to the outer wall 30. The amount of the anti-microbial agent that is put into the false lumen 40 should be sufficient to ensure that the anti-microbial agent is delivered from the false lumen 40 through the inlet lumen and outlet lumen and finally onto the outer wall 30 of the medical device. FIG. 3 shows the egress of the anti-microbial agent from the false lumen 40 through the first active lumen 50 (or the inlet lumen) and the second active lumen 60 (or the outlet lumen) and onto the outer wall 30 of the catheter. FIG. 4 also shows the egress of the anti-microbial agent from the false lumen 40 through the first active lumen 50 and onto the outer wall 30 of the catheter. An advantage of this design is to prevent contact of the substrate 100 comprising the anti-microbial agent with blood in the active lumen and eliminate the need to remove the substrate 100 from the false lumen 40 during dialysis treatments.

In order to allow diffusion of the anti-microbial agent through the false lumen wall 90 and the outer wall 30, these walls should be made from a semi-permeable material, preferably a polymer. Semi-permeable materials or polymers allow for the selective diffusion of the anti-microbial agent or other substance through these materials or polymers.

The semi-permeable material may include polymers such as, but not limited to, polyurethane, polycarbonate, silicone, ethylvinylacetate, and co-polymers thereof. The semi-permeable material may be prepared in any suitable manner as known by one skilled in the art. Suitable methods include, but are not limited to, extrusion and molding.

Furthermore, a biologically active material may be disposed as a coating on the walls defining the active lumens or disposed within the walls defining the active lumens. Any suitable biologically active materials may be used. The term "biologically active material" encompasses therapeutic agents, such as drugs, and also genetic materials and biological materials. Suitable genetic materials include DNA or RNA, such as, without limitation, DNA/RNA encoding a useful protein and DNA/RNA intended to be inserted into a human body including viral vectors and non-viral vectors. Suitable viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Suitable non-viral vectors include artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

Suitable biological materials include cells, yeasts, bacteria, proteins, peptides, cytokines and hormones. Examples of suitable peptides and proteins include growth factors (e.g., FGF, FGF-1, FGF-2, VEGF, Endotherial Mitogenic Growth Factors, and epidermal growth factors, transforming growth factor α and β, platelet derived endothelial growth factor, platelet derived growth factor, tumor necrosis factor α, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Biologically active material also includes non-genetic therapeutic agents, such as: anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, antithrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides; vascular cell growth promotors such as growth factors, Vascular Endothelial Growth Factors (FEGF, all types including VEGF-2), growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents, vasodilating agents, and agents which interfere with endogenous vasoactive mechanisms; anti-oxidants, such as probucol; antibiotic agents, such as penicillin, cefoxitin, oxacillin, tobranycin; angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

Other preferred biologically active materials include nitroglycerin, nitrous oxides, antiobitics, aspirins, digitalis, and glycosides.

The amount of the biologically active material present on or within the wall defining the first active lumen 50 can be adjusted to meet the needs of the patient. In general, the amount of the biologically active material used may vary depending on the application or biologically active material selected. One of skill in the art would understand how to adjust the amount of a particular biologically active material to achieve the desired dosage or amount.

Figure 5:
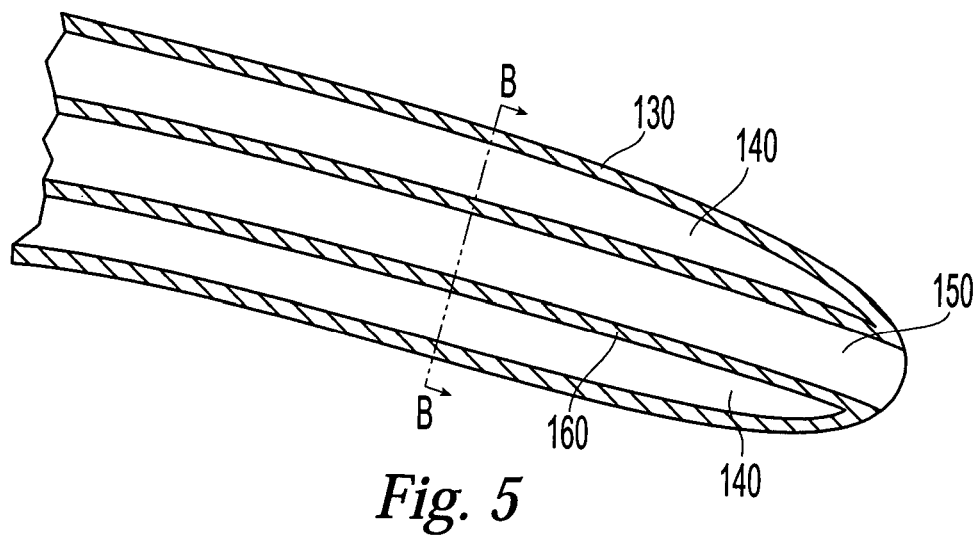
FIG. 5 illustrates a cross-sectional view along the longitudinal axis of a distal portion of a medical device of the present invention. The medical device is a catheter that comprises a first active lumen defined by an active lumen wall. The active lumen wall comprises a non-permeable polymer. A false lumen comprising an anti-microbial agent surrounds the active lumen wall and is defined by an outer lumen wall. A semi-permeable polymer forms the outer lumen wall of the catheter.
Figure 6:
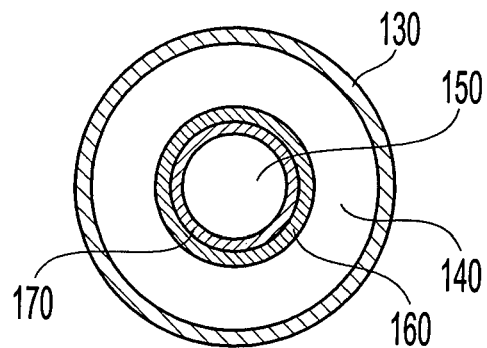
FIG. 6 shows a cross-sectional view of FIG. 5 at line B-B.
Figure 7:
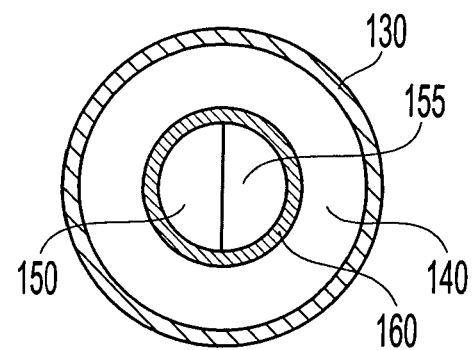
FIG. 7 shows a cross-sectional view of a medical device of the present invention wherein a false lumen surrounds a first active lumen and a second active lumen. The medical device is a catheter that comprises two active lumens defined by an active lumen wall. The active lumens include a first active lumen and a second active lumen. The active lumen wall comprises a non-permeable polymer. A false lumen comprising an anti-microbial agent surrounds the active lumen wall and is defined by an outer lumen wall. A semi-permeable polymer forms the outer lumen wall of the catheter.

In another embodiment, an active lumen wall 160 separates the false lumen 140 from the active lumen the false lumen 140 as shown in FIGS. 5-7. The active lumen wall 160 comprises a non-permeable material. Such materials do not allow the diffusion of materials through them. Thus, the non-permeable material comprises a material capable of preventing the diffusion of the anti-microbial agent into the first active lumen 150. By preventing the anti-microbial agent from entering the active lumen, more anti-microbial agent can be delivered to the outer wall 130 from the false lumen 140. Preferably, the non-permeable material comprises a polymeric material. Suitable polymeric materials include, but are not limited to, polyethylene terephthalate (PET), polyethylene teraphtalate glycol (PETG), and polystyrene. The non-permeable material may be prepared in any suitable manner as known by one skilled in the art.

Preferably, the false lumen 140 surrounds the active lumen as shown in FIGS. 5-7. The false lumen 140 and the first active lumen 150 may be concentric as shown in FIG. 6. FIG. 6 is a cross-sectional view of FIG. 5 along the line B-B. The false lumen 140 is defined by the outer wall 130 of the medical device which comprises a semi-permeable polymer. Also, there can be more than one active lumen disposed within the false lumen 140. These lumens can be concentric with some or all of the other active lumens and the false lumen 140. Alternatively, these other active lumens may not be concentric with each other or the false lumen 140.

FIG. 7 shows a cross-sectional view of a medical device having a false lumen 140 surrounding a first active lumen 150 and a second active lumen 155. An active lumen wall 160 surrounds the first active 150 and the second active lumen 155.

An anti-microbial agent, as described above, is disposed in the false lumen 140. Also as discussed above, the anti-microbial agent may be dispersed in a substrate 100 such as a polymer.

Preferably, an aqueous solution is also contained in the false lumen 140, as described above. In addition, the first active lumen 150 is preferably substantially free of the anti-microbial agent and the false lumen 140 is substantially free of the biologically active material that may be disposed in the first active lumen 150.

FIG. 5 illustrates this embodiment of the present invention. In this figure, a cross-sectional view along the longitudinal axis of the distal portion 20 of a catheter is shown. FIG. 6 illustrates a cross-sectional view of FIG. 5 at lines B-B. As shown in the figures, the catheter comprises a first active lumen 150 defined by an active lumen wall 160 comprising a non-permeable material. A coating 170 comprising a biologically active material is disposed on the active lumen wall 160 as shown in FIG. 6. Alternatively, the biologically active material may be disposed within the active lumen wall 160. A false lumen 140 containing an anti-microbial agent surrounds the first active lumen 150. A semi-permeable material defines the false lumen 140 and forms the outer wall 130 of the catheter. The non-permeable polymer of the active lumen wall 160 prevents the diffusion and mixing of the anti-microbial agent with the biologically active agent present in the coating 170 within the active lumen wall 160 of the first active lumen 150. The semi-permeable material allows for the controlled diffusion of the anti-microbial agent from the false lumen 140 to the outer wall 130 of the catheter. In this embodiment, the semi-permeable outer wall 130 can be formed in any suitable matter. For example, the material of the outer wall 130 can be made from one or more semi-permeable materials, or made from permeable or nonpermeable materials in which pores are physically created.

The present invention also provides for methods of assembling the medical devices described above. In one embodiment, the method comprises obtaining a medical device having a portion that is insertable into the body of a patient. The medical device, such as a catheter, includes an outer wall 30, a false lumen 40, and a first active lumen 50 as described above. The method also comprises obtaining a substrate 100 comprising an anti-microbial agent and having a first end 110 and a second end 120 as described above. The first end 110 of the substrate 100 is inserted into the false lumen 40 such that the first end 110 is positioned closer to the distal portion 44 of the false lumen 40 than the second end 120. The substrate 100 may be inserted into the false lumen 40 of the medical device during manufacture or after insertion of the medical device into the body. The method may also include filling the false lumen 40 with an aqueous solution and exposing the anti-microbial agent therein to the aqueous solution.

In use, the medical device is introduced into a body lumen in a manner known to the skilled artisan. The medical device can be inserted into the body of a patient so that it contacts any surface of a body lumen. Such body lumen include blood vessels, urinary tract, coronary vasculature, esophagus, trachea, colon, and biliary tract. The medical device may also be inserted through the skin, nose, eyes, breast duct, or ears.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

What is claimed is:

1. A medical device with anti-microbial properties comprising:
    a catheter having a portion that is partially insertable into the body of a patient and accessible from outside the body once the portion is inserted, wherein the portion has an outer wall, a first and a second active lumen within the outer wall, and a false lumen within the outer wall, and wherein the false lumen has a distal portion and a proximal portion, the false lumen contains an anti-microbial agent that provides the outer wall with anti-microbial properties, the distal portion of the false lumen is sealed to prevent the anti-microbial agent contained therein from directly entering into the body or bloodstream, and the first active lumen and the second active lumen at least partially surround the false lumen, and wherein the anti-microbial agent comprises an iodine-based substance.

2. The medical device of claim 1, wherein the first and second active lumens and the false lumen are concentric.

3. The medical device of claim 1, wherein the first active lumen is an inlet lumen and the second active lumen is an outlet lumen, and the catheter is a dialysis catheter.

4. The medical device of claim 1 further comprising a biologically active material disposed in at least one of the first and second active lumens.

5. The medical device of claim 1, wherein the false lumen contains an aqueous solution therein.

6. The medical device of claim 1, wherein the false lumen contains a substrate having a first end and a second end, wherein the substrate comprises said anti-microbial agent.

7. The medical device of claim 1, wherein the substrate is in the shape of a rod.

8. The medical device of claim 1, wherein the first end of the substrate comprises an amount of anti-microbial agent that is greater than the amount of anti-microbial agent present in the second end of the substrate.

9. A medical device with anti-microbial properties comprising:
a catheter having a portion that is partially insertable into the body of a patient and accessible from outside the body once the portion is inserted, wherein the portion has an outer wall, a first active lumen and a second active lumen within the outer wall, and a false lumen within the outer wall, and wherein the false lumen has a distal portion and a proximal portion, the false lumen contains an anti-microbial agent that provides the outer wall with anti-microbial properties, the distal portion of the false lumen is sealed to prevent the anti-microbial agent contained therein from directly entering into the body or bloodstream, and the first and second active lumens at least partially surround the false lumen, wherein the first active lumen is an inlet lumen and the second active lumen is an outlet lumen, and the catheter is a hemodialysis catheter.

10. The medical device of claim 9 further comprising a biologically active material disposed in at least one of the first and second active lumens.

11. The medical device of claim 9, wherein the false lumen contains a substrate having a first end and a second end, wherein the substrate comprises said anti-microbial agent.

12. The medical device of claim 9, wherein the substrate is in the shape of a rod.

13. The medical device of claim 9, wherein the first end of the substrate comprises an amount of anti-microbial agent that is greater than the amount of anti-microbial agent present in the second end of the substrate.

14. The medical device of claim 9, wherein the false lumen contains an aqueous solution therein.

15. A medical device with anti-microbial properties comprising:
a portion that is partially insertable into the body of a patient and accessible from outside the body once the portion is inserted, wherein the portion has an outer wall, at least one active lumen within the outer wall, and a false lumen within the outer wall, and wherein the false lumen has a distal portion and a proximal portion, and the distal portion of the false lumen is sealed to prevent the anti-microbial agent contained therein from directly entering into the body or bloodstream; and
a substrate having a first end and a second end, wherein the substrate is comprised of an anti-microbial agent, the substrate is capable of being inserted into the false lumen, and the substrate is capable of providing the outer wall with anti-microbial properties, wherein the anti-microbial agent is an iodine-based substance, wherein the portion has a first active lumen and a second active lumen and wherein the first active lumen and the second active lumen at least partially surround the false lumen.

16. The medical device of claim 15, wherein the medical device is a catheter.

17. The medical device of claim 15, wherein the substrate is in the shape of a rod.

18. The medical device of claim 15, wherein the first end of the substrate comprises an amount of anti-microbial agent that is greater than the amount of anti-microbial agent present in the second end of the substrate.

19. The medical device of claim 15, wherein the at least one active lumen and the false lumen are concentric.

20. The medical device of claim 15, wherein the first active lumen is an inlet lumen and the second active lumen is an outlet lumen, and the catheter is dialysis catheter.

21. A hemodialysis catheter with anti-microbial properties comprising:
a portion that is partially insertable into the body of a patient and accessible from outside the body once the portion is inserted, wherein the portion has an outer wall, at least one active lumen within the outer wall, and a false lumen within the outer wall, and wherein the false lumen has a distal portion and a proximal portion, and the distal portion of the false lumen is sealed to prevent the anti-microbial agent contained therein from directly entering into the body or bloodstream; and
a substrate having a first end and a second end, wherein the substrate is comprised of an anti-microbial agent, the substrate is capable of being inserted into the false lumen, and the substrate is capable of providing the outer wall with anti-microbial properties, wherein the portion has a first active lumen and a second active lumen, and the first active lumen and the second active lumen at least partially surround the false lumen.

22. The medical device of claim 21 further comprising a biologically active material disposed in at least one of the first and second active lumens.

23. The medical device of claim 21, wherein the substrate is in the shape of a rod.

24. The medical device of claim 21, wherein the first end of the substrate comprises an amount of anti-microbial agent that is greater than the amount of anti-microbial agent present in the second end of the substrate.

25. The medical device of claim 21, wherein the at least one active lumen and the false lumen are concentric.

26. The medical device of claim 21, wherein the first active lumen is an inlet lumen and the second active lumen is an outlet lumen, and the catheter is dialysis catheter.

* * * * *